(12) United States Patent
Koeppel et al.

(10) Patent No.: US 7,481,819 B2
(45) Date of Patent: Jan. 27, 2009

(54) COMPACT MULTI-USE LANCING DEVICE

(75) Inventors: Bradley Koeppel, Smyrna, GA (US);
William E. Conway, Smyrna, GA (US);
Brian Vanhiel, Smyrna, GA (US); Jack Griffis, Decatur, GA (US); David R. Buenger, Roswell, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 0 days.

(21) Appl. No.: 10/598,439

(22) PCT Filed: Mar. 2, 2005

(86) PCT No.: PCT/US2005/006519

§ 371 (c)(1),
(2), (4) Date: Jun. 28, 2007

(87) PCT Pub. No.: WO2005/084557

PCT Pub. Date: Sep. 15, 2005

(65) Prior Publication Data

US 2007/0255302 A1    Nov. 1, 2007

Related U.S. Application Data

(60) Provisional application No. 60/549,317, filed on Mar. 2, 2004.

(51) Int. Cl.
*A61B 17/32*    (2006.01)
(52) U.S. Cl. .................................. 606/182; 606/181

(58) Field of Classification Search ................. 606/181, 606/182, 184, 183, 185; 600/583
See application file for complete search history.

(56) References Cited

U.S. PATENT DOCUMENTS

| | | | | |
|---|---|---|---|---|
| 4,064,871 A | * | 12/1977 | Reno ........................... | 600/369 |
| 4,442,836 A | * | 4/1984 | Meinecke et al. ........... | 606/182 |
| 4,449,529 A | * | 5/1984 | Burns et al. ................. | 606/182 |
| 4,527,561 A | * | 7/1985 | Burns .......................... | 606/182 |
| 4,628,929 A | * | 12/1986 | Intengan et al. ............. | 606/182 |
| 4,735,203 A | * | 4/1988 | Ryder et al. ................. | 606/182 |
| 5,356,420 A | * | 10/1994 | Czernecki et al. ........... | 606/182 |
| 5,476,474 A | * | 12/1995 | Davis et al. ................. | 606/182 |
| 5,529,581 A | * | 6/1996 | Cusack ........................ | 606/181 |
| 5,645,555 A | * | 7/1997 | Davis et al. ................. | 606/182 |
| 5,908,434 A | * | 6/1999 | Schraga ....................... | 606/181 |
| 6,010,519 A | * | 1/2000 | Mawhirt et al. ............. | 606/181 |
| 6,190,398 B1 | * | 2/2001 | Schraga ....................... | 606/181 |
| 6,221,089 B1 | * | 4/2001 | Mawhirt ...................... | 606/181 |
| 6,409,740 B1 | * | 6/2002 | Kuhr et al. ................... | 606/182 |
| 6,949,111 B2 | * | 9/2005 | Schraga ....................... | 606/182 |
| 7,160,313 B2 | * | 1/2007 | Galloway et al. ............ | 606/167 |

\* cited by examiner

*Primary Examiner*—Darwin P Erezo
(74) *Attorney, Agent, or Firm*—Gardner Groff Greenwald & Villanueva, PC

(57) ABSTRACT

A multi-use micro-sampling or lancing device (10) having an outer housing (12), a lancet holder (32) that engages a lancet (30) and constrains the lancet along a controlled and predefined path of travel during the lancing stroke, and a drive mechanism with a pair of opposed, off axis torsion springs (80,82) working in tandem to drive and return the lancet holder through its lancing stroke.

19 Claims, 6 Drawing Sheets

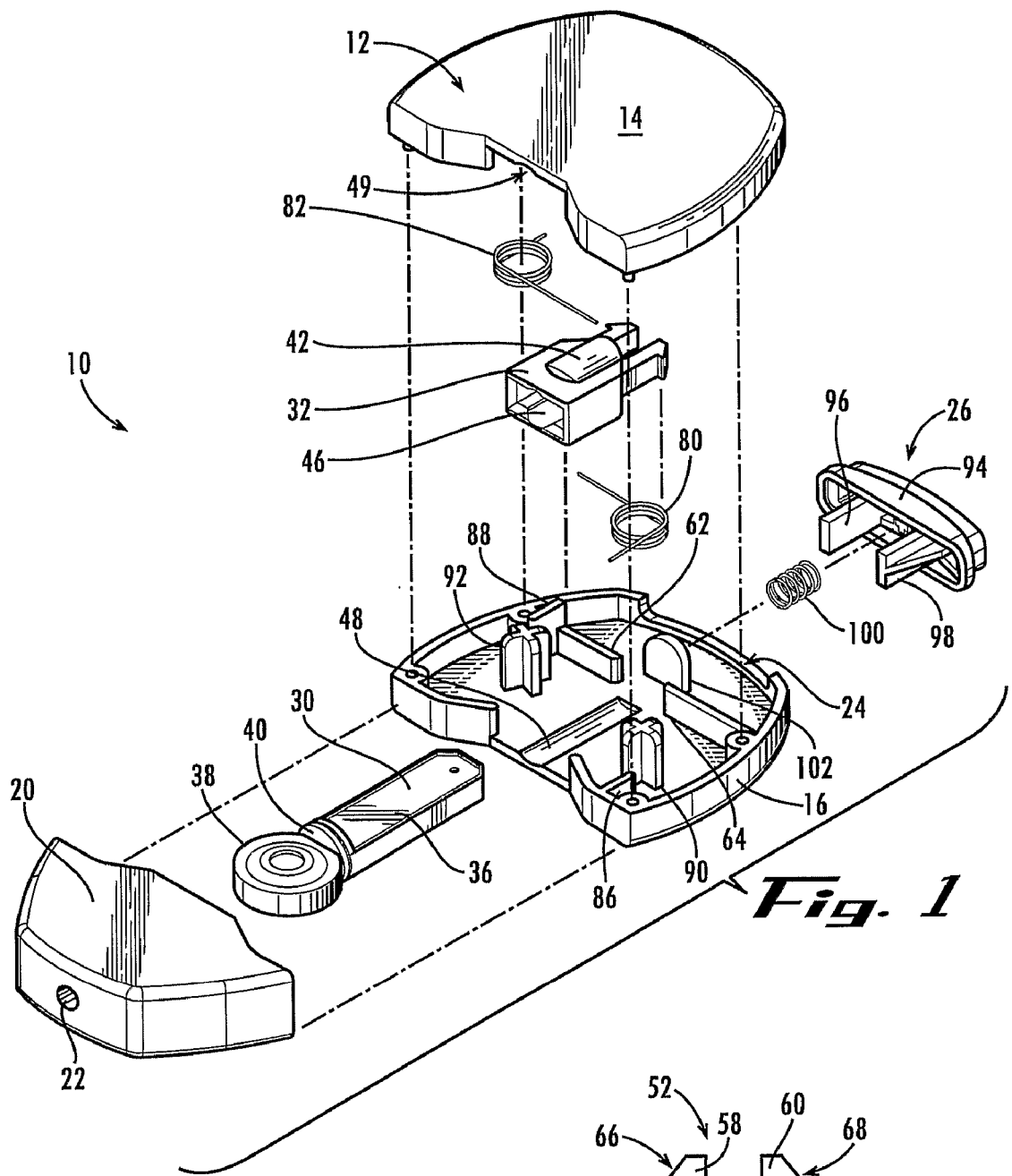
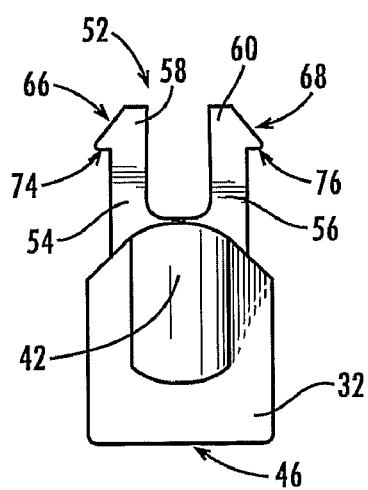

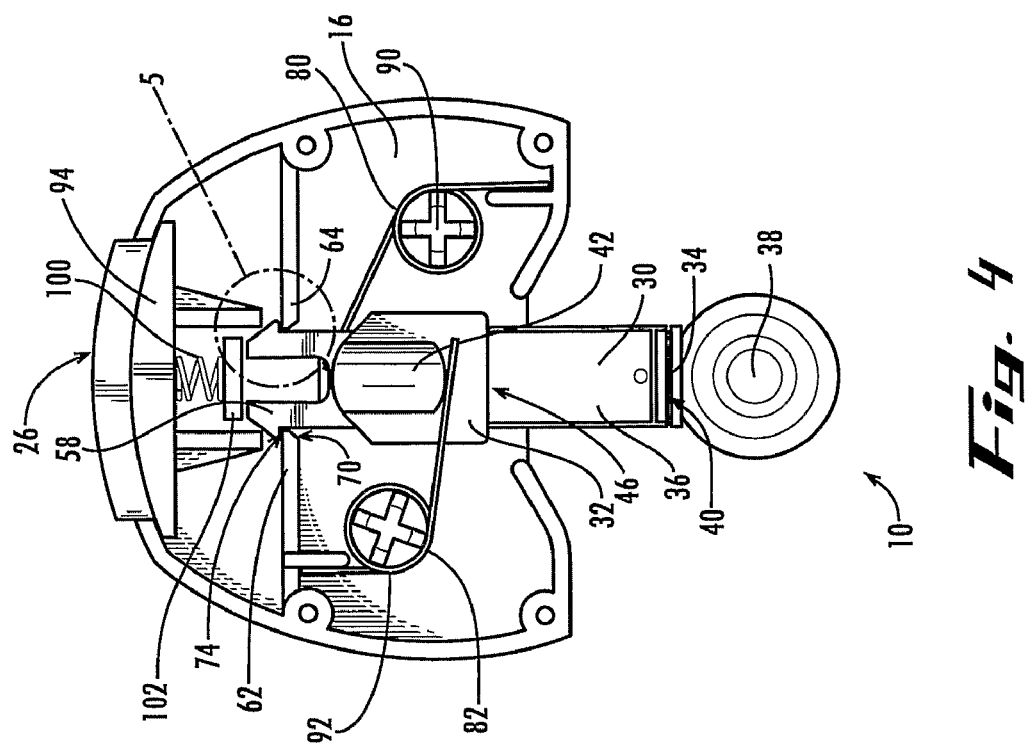
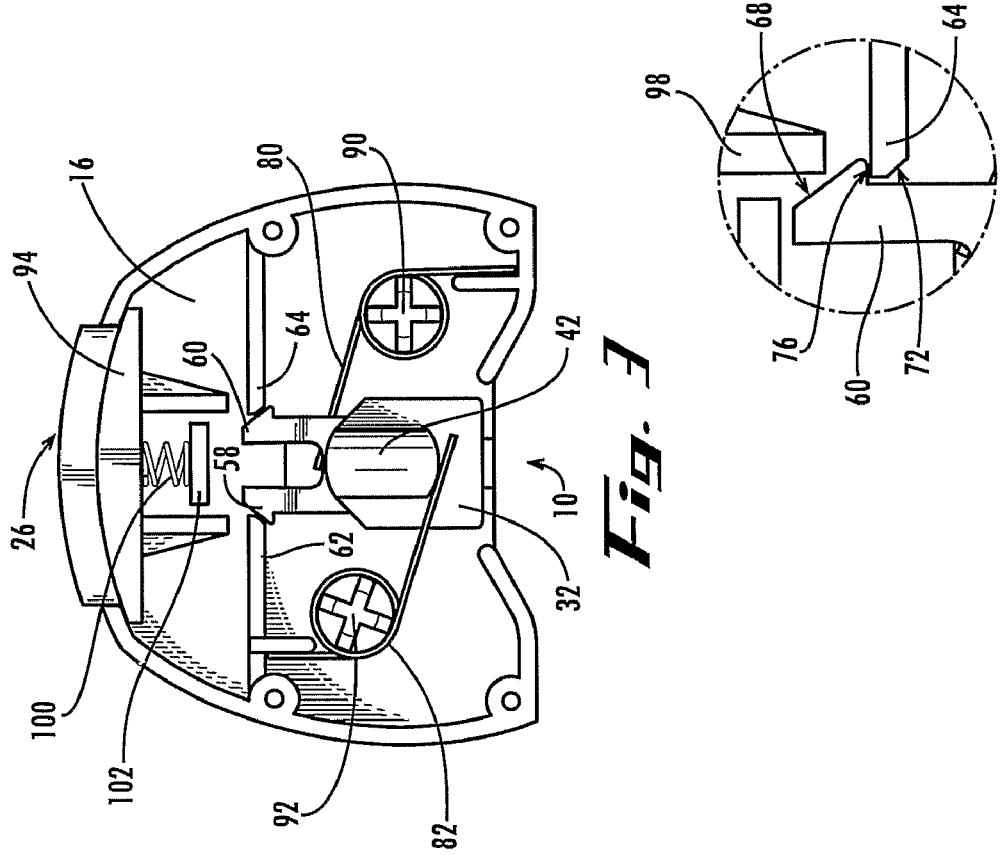

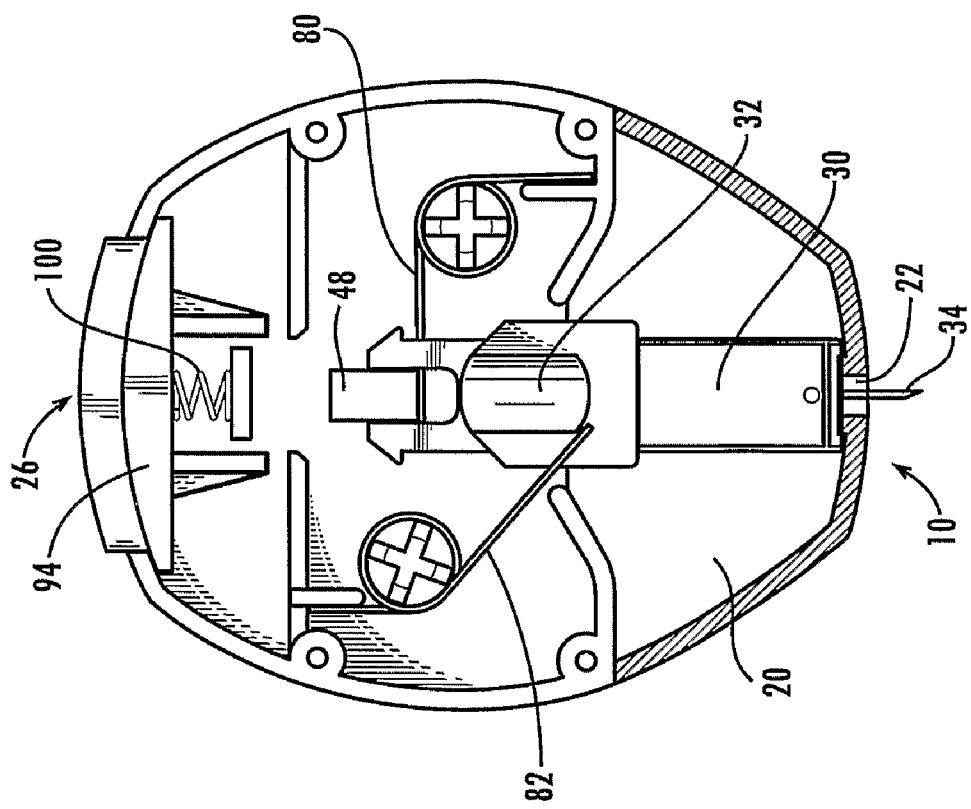
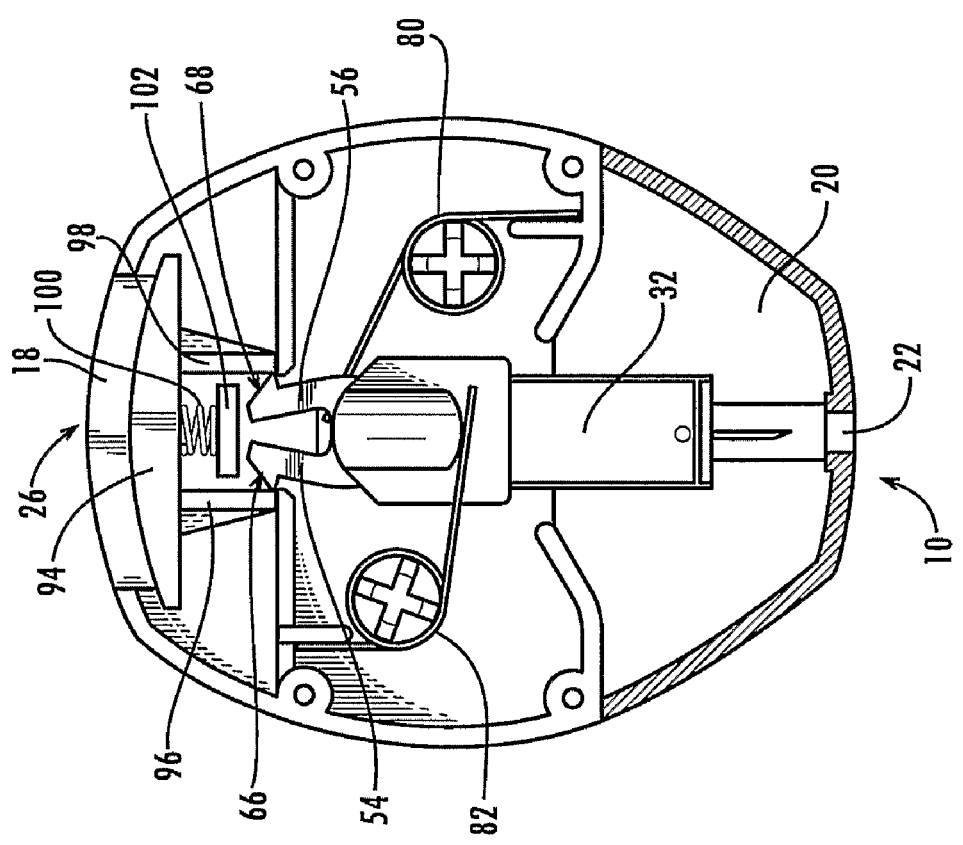

COMPACT MULTI-USE LANCING DEVICE

CROSS-REFERENCE TO RELATED APPLICATION

This application is a U.S. National Phase of International Application No. PCT/US2005/006519, filed Mar. 2, 2005, which in turn claims the benefit of U.S. Provisional Patent Application Ser. No. 60/549,317, filed Mar. 2, 2004, the entireties of which applications are hereby incorporated herein by reference for all purposes.

TECHNICAL FIELD

The present invention relates generally to medical devices and procedures, and more particularly to a multi-use, micro-sampling device.

BACKGROUND OF THE INVENTION

Many medical procedures require puncturing of the skin, and sometimes underlying tissues, of an animal or human subject. For example, a sharp lancet tip is commonly used to puncture the subject's skin at a lancing site to obtain a sample of blood, interstitial fluid or other body fluid, as for example in blood glucose monitoring by diabetics and in blood typing and screening applications.

In some instances, a person must periodically sample their blood for multiple testing throughout the day or week. Thus, due to the nature of micro-sampling for blood glucose monitoring, many individuals requiring regular monitoring prefer to do so discretely. Current multi-use micro-sampling devices tend to have a large, pen-like form that restricts the ability of the individual user to conduct micro-sampling discretely. Some have attempted to miniaturize the micro-sampling device, but the device still has a large and indiscrete size.

Thus it can be seen that needs exist for improvements to lancing devices to provide a micro-sampling device having a small and discrete size. Needs further exist for such a mechanism that has a smaller overall profile while remaining compatible with standard lancets commonly available. In addition, needs exist for combining drive elements for control of the lancet travel and return that provide for a wide, yet far shorter, overall shape.

SUMMARY OF THE INVENTION

Briefly described in example forms, the present invention is a multi-use micro-sampling or lancing device comprising a compact outer housing containing drive and activation mechanisms for receiving a disposable and replaceable lancet and for driving the lancet through a controlled lancing stroke for sample collection. The housing preferably includes a lancet holder that securely but releasably engages the lancet and constrains the lancet along a controlled and pre-defined path of travel during the lancing stroke.

The lancing device preferably includes a drive mechanism including a pair of opposed torsion springs to drive and propel the lancet through an extended position along its lancing stroke, and to return the lancet to a retracted position fully within the housing. This drive mechanism is compact, and thus, the overall size, and particularly the length, of the lancing device can be significantly reduced. The lancing device may, for example, have the overall size and shape of a typical automotive door-lock remote control keyfob.

In one aspect, the invention comprises a lancing device having a compact housing, a lancet holder for a holding a lancet and mounted for back and forth movement along a lancing stroke path within the housing, and a drive mechanism comprising at least one off-axis spring coupled to the lancet holder, the at least one off-axis spring being positioned laterally offset from the lancing stroke path of the lancet holder. In an example embodiment, the at least one spring comprises a drive spring for driving the lancet holder along the lancing stroke and an opposing return spring for returning the lancet holder.

Preferably, the compact housing has a width comparable to the length of the housing and is about twice as long as a lancet used therein. Additionally, the lancing device has a trigger to trigger the lancing stroke. Also preferably, the lancet holder is barbed to hold the lancet holder in a ready position, ready for triggering, wherein the barbed lancet holder comprises compression arms each having at least one chamfered barb, and wherein the trigger engages the chamfered barbs to trigger the lancing stroke.

In another aspect, the present invention is a lancing device having a compact housing having a length and a width, with the length of the housing being roughly the same as the width of the housing; and a drive mechanism within the housing for driving a lancet along a pre-defined path. The drive mechanism includes a carrier for securely holding the lancet, a first spring for urging the lancet from an initial position into an extended position wherein a portion of the lancet protrudes out of the compact housing, and a second spring for retracting the lancet back into the housing. Preferably, the springs are positioned laterally offset from the pre-defined path.

In yet another aspect, the present invention is a lancing device having a compact, non-elongated, puck-like housing, a drive mechanism for movably supporting a lancet along a lancing stroke, a trigger for triggering the drive mechanism, and wherein the housing has a length of between about two and four times as long as the length of the lancet used therein. Preferably, the housing is about twice as long as the lancet, and has a width roughly equal to its length. Also preferably, the drive mechanism includes off-axis springs for urging the lancet back and forth along the lancing stroke, the off-axis springs being laterally offset from the lancing stroke.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 2 is a top view of a lancet holder component of the multi-use lancing device of FIG. 1.

FIG. 3 is a top sectional view of the multi-use lancing device of FIG. 1 shown prior to the insertion of a lancet, and with the endcap removed.

FIG. 4 is a top sectional view of the multi-use lancing device of FIG. 1 shown having a lancet inserted therein, and with the drive mechanism in its extended "ready" configuration.

FIG. 5 is a detailed view of the inter-engaging locking elements of the lancet holder of FIG. 4.

FIG. 7 is a top sectional view of the multi-use lancing device of FIG. 1, shown with its endcap portion attached and having a lancet in the ready position.

FIG. 8 is a top sectional view of the multi-use lancing device of FIG. 1, showing as the device is activated to release the drive mechanism from its ready state.

FIG. 9 is a top sectional view of the multi-use lancing device of FIG. 1, shown with the lancet in its extended position wherein the lancet tip projects outwardly from the device's housing.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
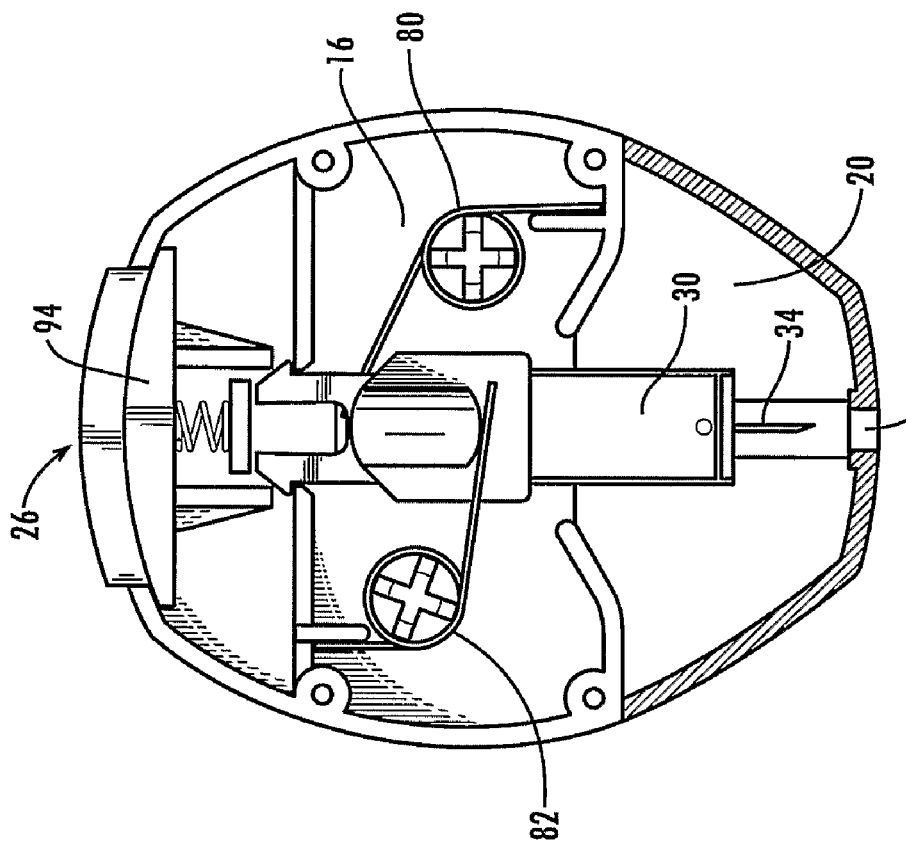
FIG. 1 is an assembly view of a multi-use lancing device according to an example embodiment of the present invention.

With reference now to the drawing figures, FIG. 1 is an assembly view of a multi-use micro-sampling device or lancing device 10 according to an example embodiment of the present invention. The lancing device 10 preferably comprises a housing 12 having a top portion 14 connected to a bottom portion 16, as by adhesive or crush-pins. An endcap portion 20 of the lancing device 10 is removably connected to the housing 12 such that a new lancet can be manually inserted into the device and a used lancet can be manually removed from the device. The endcap portion 20 preferably defines a small opening 22 for protrusion of a sharp lancet needle or tip therethrough and into the tissue at the intended lancing site selected by user. At the end of the housing 12 opposite the endcap portion 20 is an opening or channel 24 for receiving an activating button assembly 26 and for guiding the activating button assembly along a pre-defined path of travel.

A replaceable and disposable lancet 30 is installed in a reciprocating lancet holder, carrier, or sled 32 within the housing. The lancet 30 itself is translationally mounted within the housing 12 for reciprocating movement. The lancet 30 typically comprises a needle or blade forming a sharp lancet tip 34 (see FIGS. 4 and 7, for example) and a lancet body 36, and is positioned such that the tip 34 is directed forward, toward the lancet opening 22 in the endcap portion 20. Preferably, the lancet body 36 is formed of plastic, and is injection-molded around the needle or blade. The lancet tip 34 is preferably encapsulated by a protective sterility cap 38, which is integrally molded with the lancet body 36 and forms a sterility and safety barrier for the lancet tip. As shown in FIG. 1, the protective sterility cap 38 of each lancet 30 is releasably connected to the lancet body 36 at a transition region 40, which is an area of weakening such that it is easily detached and removed from the lancet body 36. The lancet 30 can be, for example, a standard, commercially-available lancet such as an Accu-Check® Softclix® lancet.

As more clearly seen in FIG. 2, the lancet holder 32 preferably comprises two male guide elements, such as upper guide element 42 (for clarity, only one of which is shown) and an opening 46 at one end of the lancet holder 32. The opening 46 is sized and shaped to securely but releasably hold the replaceable lancet 30. Preferably, the male guide elements are integrally formed on both the upper and lower surfaces of the lancet holder 32, and slide within inter-engaging female guide surfaces 48, 49, such as grooves or channels, formed in the lower and upper portions 16 and 14 of the housing 12, to constrain the lancet 30 along a controlled and pre-defined path of travel during the lancing stroke. For clarity, only one of the male guide elements 42 is shown in the figures, and it will be understood by those skilled in the art, that a female guide surface 49 on the underside of the top portion of the housing 14 receives and guides the male portion 42. Another male guide element (not shown) on the underside of the lancet holder 32 engages with female guide surface 48. It will be understood by those skilled in the art that a single pair of cooperating guide elements can be used or two or more such pairs can be used. Thus, while two pairs of guide elements are shown, fewer or more such pairs can be utilized as described.

The lancet holder 32 preferably has a generally U-shaped portion 52 formed by an opposed pair of compression arms 54 and 56, with chamfered barbs 58 and 60 formed at their distal ends, respectively, for engaging cooperating retaining or locking tabs 62 and 64 integrated within the bottom portion 14 of the housing 12. The retaining tabs 62 and 64 engage the barbs 58 and 60 to maintain lancet holder 32 in a "ready" position against the bias force of the drive spring when the device 10 is cocked. The ends of the retaining tabs 62 and 64 preferably define chamfers 70 and 72 for sliding contact along cooperating chamfered faces 66 and 68 of the barbs 58 and 60, to provide a smooth cocking action. The compression arms 54 and 56 can resiliently flex inwardly and thus allow movement of their free ends towards each other upon cocking and firing of the device 10. The barbs 58 and 60 have flat edges 74 and 76 for releasable engagement against the retaining tabs 62 and 64 in the ready position.

Preferably, the retaining tabs 62 and 64 are relatively rigid and the compression arms 54, 56 are flexible. Alternatively, the retaining tabs 62, 64 could be made flexible and the arms 54, 56 could be relatively inflexible (the firing being accomplished by deflecting the retaining tabs). Moreover, both the compression arms and the retaining tabs could be flexible.

Referring now to FIGS. 1, 3, 4, 6, 7, 8, 9, and 10, two torsion springs, namely a drive spring 80 and a return spring 82, operate to drive and return the lancet holder 32 along the lancing stroke upon triggering of the lancing device 10. Together, the drive spring 80, the return spring 82, and the lancet holder 32 form a drive mechanism 84 for driving the lancet back and forth along its pre-defined path. The drive spring 80 is the stronger of the two springs and drives the lancet 30 from its initial position into its extended position. The return spring 82 serves to retract the lancet 30 back into the housing 12 after lancing the skin. Preferably, the drive spring 80 and the return spring 82 are laterally offset from a lancing stroke of the lancet holder 32, and thus are positioned off the axis of the lancet holder so as to provide a more compact configuration of the lancing device 10. (Of course, the very tips of the springs 80 and 82 contact the lancet holder 32 along the stroke path, but the vast majority of the springs lie outside of the stroke path).

In an example embodiment of the present invention, the device 10 is puck-like and has a length in the direction of the lancing stroke of about 3.5 inches and a width, which is traverse to its length, of about 2.875 inches. The device 10 also has a thickness of about 0.5 inch. Thus, the exemplary lancing device 10 has an aspect ratio of about 1.25. The housing could be reconfigured to have an aspect ratio of less than 1.0 to about 4 or 5. Additionally, the length of the housing can be between about two and four times the length of the lancet used therein.

A pair of posts or lugs 86 and 88 serves as retainers for positioning the springs 80 and 82, and thereby more precisely defining the equilibrium position of the lancet holder 32. The springs 80 and 82 are secured within the housing 12 around a pair of axles on pivots 90 and 92, respectively, projecting from the bottom portion 14 of the housing.

The lancing device 10 preferably further comprises an activating button assembly or trigger 26 positioned at the end of the housing 12 opposite the endcap portion 20, for triggering the drive mechanism 84 to propel the lancet 30 through its lancing stroke. An example configuration of the trigger 26 preferably includes a button portion 94 having a pair of posts 96 and 98 on its inner surface which contact the chamfered faces 66 and 68 of the compression arms 54 and 56 of the lancet holder 32. When the button 94 is depressed, the posts 96, 98 press inwardly against the arms 54 and 56 to release the flat edges 74 and 76 of barbs 58 and 60 from engagement with the retaining tabs 62 and 64 to initiate (trigger) the lancing action. The trigger 26 preferably further comprises a coil spring 100, which is positioned between a spring post or stop 102 extending from bottom portion 16 of the housing 12 and the button 94, thereby biasing the button 94 outwardly.

The opposed torsion spring drive mechanism 84 permits a significant reduction in the overall size (and especially the length) of the lancing device 10, as compared to typical known lancing devices. Thus, the overall size of the lancing device 10 may be a bit wider than conventional lancing devices, but the length of the device 10 is much shorter. With this reduced size, the lancing device 10 can accommodate other elements, such as an adjustable depth-control ring (for controlling the penetration depth of the lancet into the user's skin), a lancet storage feature, or other similar optional features, without resulting in an objectionably large device.

FIG. 3 shows a top sectional view of the multi-use lancing device 10 prior to insertion of the lancet 30 therein. The lancet holder 32 is not cocked, and thus the lancet holder is considered to be in a "withdrawn" or "steady" state. In this "withdrawn" state, the activating button 94 and the coil spring 100 are fully retracted. Thus, the coil spring 100 is positioned against the spring post 102 of the bottom portion 16. The return torsion spring 82 is in a retracted compression state, or its "equilibrium" or "steady" state, and opposes the "equilibrium" or "steady" position of the drive spring 80. The drive torsion spring 80 is also in a forward compression state, or its "steady" compression state. In this position, the drive spring 80 and return spring 82 counter-balance one another, and the lancet holder 32 is in an equilibrium position.

When the device 10 is in its "equilibrium" state, a user manually loads a new lancet 30 (with its protective cap still in place) into the lancet holder 32 and pushes the lancet holder back (i.e., towards the activation button assembly 26), until the barbs 58 and 60 of the lancet holder snap into engagement with the lancet holder retaining tabs 62 and 64, thereby placing the device in its "cocked" or "ready" position. Once the device is thusly cocked, the user would remove the protective sterility cap 38.

FIG. 4 shows the lancing device 10 without the endcap portion 20 and having a lancet 30 inserted therein. The lancet 30 is shown with its protective cap 38 still connected to its body 36. The return torsion spring 82 is in its non-compressed or "relaxed" state, and the drive torsion spring 80 is in its fully-extended or "ready" state. Thus, a biasing force is applied by the extended drive spring 80 on the lancet holder 32 in the forward direction (i.e., toward the lancet tip 34). The activating button assembly 26 is in its "steady" state. As seen more clearly in FIG. 5, the flat edges 74 and 76 of the barbs 58 and 60 of the lancet holder 32 are in engagement with the retaining tabs 62 and 64, thus holding the drive mechanism 84 in its cocked or "ready" state. The user manually removes the protective sterility cap 38 from the lancet body prior to replacing the endcap 20.

Figure 6:
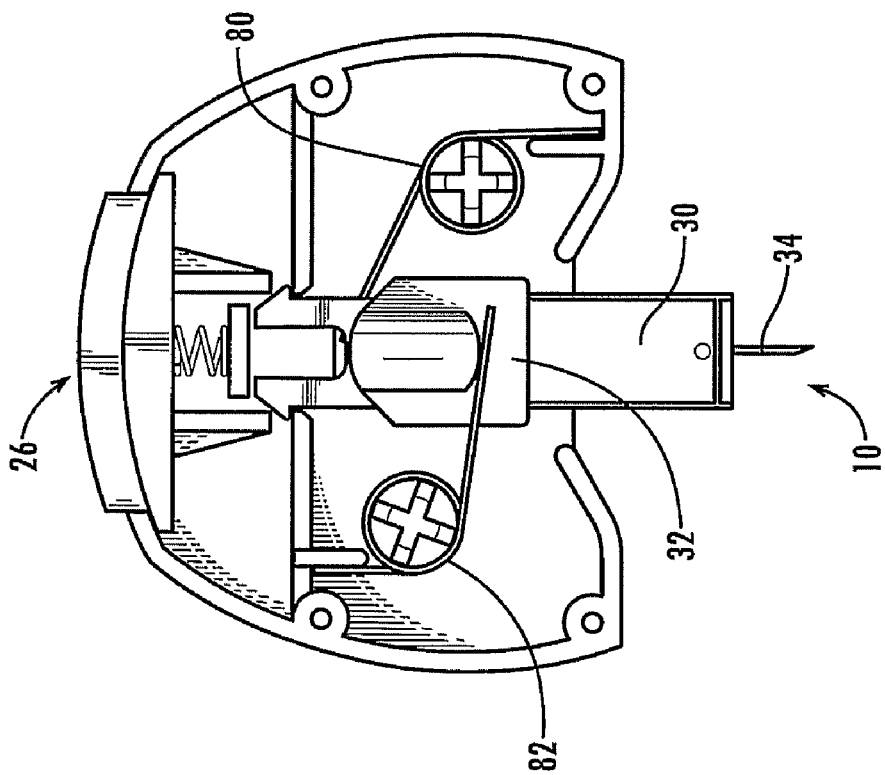
FIG. 6 is a top sectional view of the multi-use lancing device of FIG. 1 shown having a lancet inserted therein, with its protective sterility cap removed from the lancet.

FIG. 6 shows the multi-use lancing device 10 having the lancet 30 inserted therein and with its protective sterility cap 38 manually removed, thereby exposing the lancet tip 34. Once the protective sterility cap 38 has been removed, the user then replaces the endcap portion 20. FIG. 7 shows the lancing device 10 with its endcap portion 20 in place. The user then places the opening 22 of the lancing device 10 against his or her skin at the desired lancing site, and presses the button 94 to fire or "activate" the lancing device.

FIG. 8 shows the lancing device 10 as the device is being triggered or "activated". The lancing device 10 is activated when the activating button 94 is pressed. As the button 94 is pressed, the channel 24 in the housing 12 guides the movement of the activating button 94 during compression of the spring 100. Posts 96 and 98 engage the chamfered faces 66 and 68 of the compression arms 54 and 56 of the lancet holder 32, to flex the arms inwardly and release the barbs 58 and 60 from retaining tabs 62 and 64, initiating the lancing action. Because the drive spring 80 is stiffer than the return spring 82, the lancet 30 is driven forward into its extended position. The lancet 30 moves into its extended position, wherein its tip 34 punctures the user's skin at the lancing site, and then is withdrawn back to a retracted position where the tip is shielded within the housing 12.

FIG. 9 shows the lancing device 10 with the lancet tip 34 in its extended position, projecting through the opening 22 of the endcap portion 20. The lancet 30 and the lancet holder 32 are in their fully extended positions when the male guide element 42 of the lancet holder 32 traverses the length of the cooperating female portion 48, and consequently, a forward face of the lancet body 36 contacts an inner surface 104 of the endcap portion 20. In alternate embodiments, the endcap 20 optionally includes a depth adjustment mechanism (unshown) permitting the user to selectively vary the position of the stop surface 104. Upon release of the activating button assembly 26 the retraction spring 100 biases the activating button 94 back to its initial position. The return torsion spring 82 is extended, and the drive spring 80 is relaxed, thereby imparting a force to bias the lancet holder 32 back toward its withdrawn position. Once the lancing procedure is completed, the tip 34 of the lancet 30 is drawn back into the lancing device 10, and the user removes the lancing device from the lancing site so as to obtain a sampling of blood or other bodily fluid.

Figure 10:
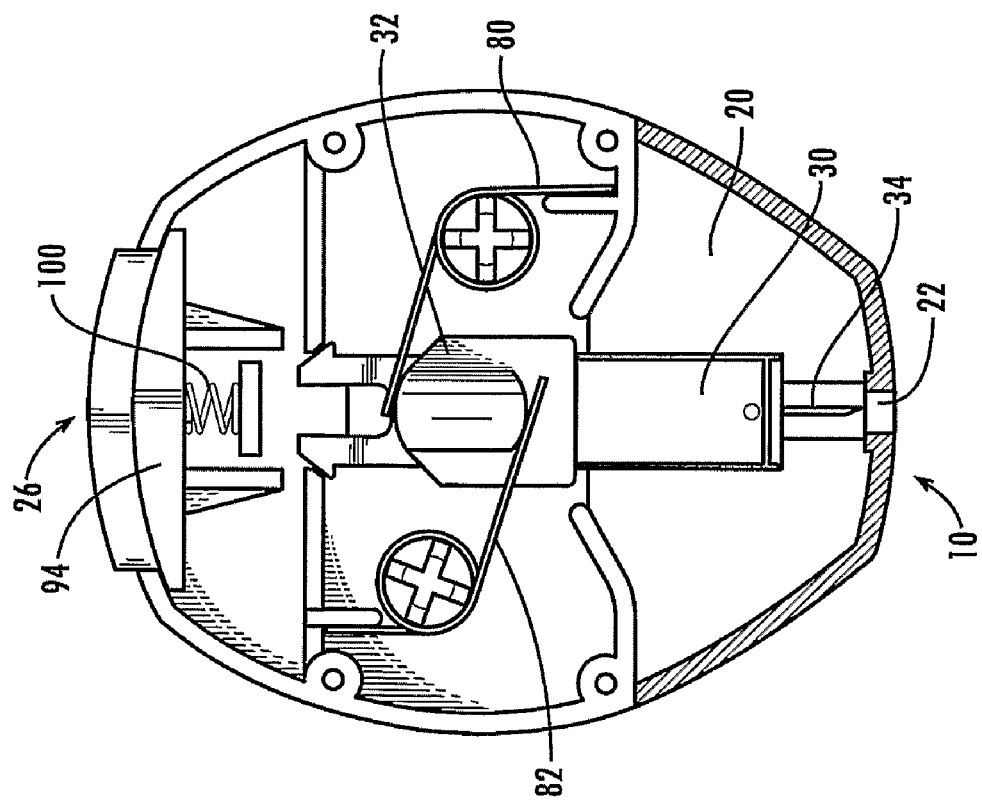
FIG. 10 is a top sectional view of the multi-use lancing device of FIG. 1, shown with a used lancet drawn back into its retracted position with the sharp lancet tip fully contained within the housing.

FIG. 10 shows the multi-use lancing device 10 with the used lancet 30 drawn back into its withdrawn position, fully within the housing. The springs 80 and 82 have returned to their equilibrium or "steady" state. The endcap portion 20 of the lancing device 10 can now be detached so that the used lancet 30 can be removed and a new lancet can be inserted. As seen in FIG. 9, the activating button assembly 26 including the retraction spring 100 has returned to its "steady" state such that the activating button 94 is fully retracted.

Figure 11:
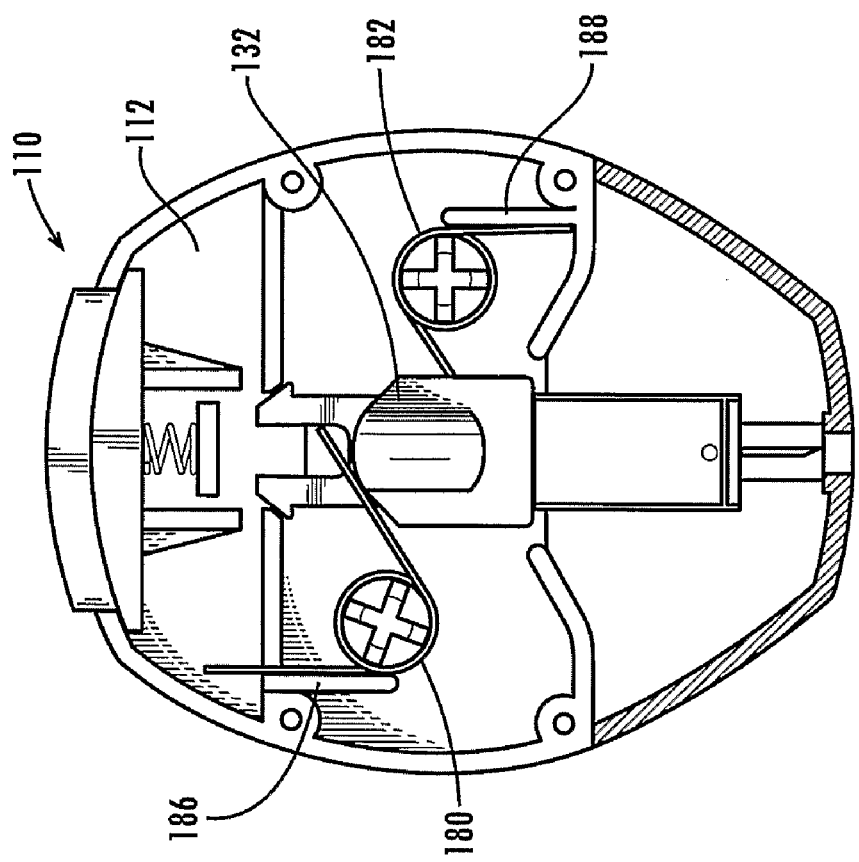
FIG. 11 is a top sectional view of a multi-use lancing device according to another example embodiment of the present invention.

FIG. 11 shows a multi-use lancing device 110 according to another example embodiment of the present invention. The lancing device 110 is substantially similar to the lancing device 10 with the exception of the orientations of the drive torsion spring 180 and return torsion spring 182. The lancet holder 132 is shown in its "steady" state, with springs 180 and 182 in equilibrium. When the device 110 is cocked to place the lancet holder 132 in the ready position, the drive spring 180 is compressed to apply force on the lancet holder in the forward direction, and the return spring 182 is relaxed. When the device 110 is activated to release the lancet holder 132 and the lancet moves to its extended position, the return spring 182 is compressed to apply rearward force on the lancet holder 132, and the drive spring 180 is relaxed. The springs 180 and 182 then return to equilibrium with the lancet holder 132 back in its retracted position within the housing 112. Thus, in the device of FIG. 11, the energized states of the drive torsion spring 180 and the return torsion spring 182 are compressed in the "coil" directions to provide biasing force on the lancet holder 132; whereas in FIGS. 1-10, the energized states of the springs 80 and 82 are extended in the "reverse coil" directions. A pair of posts or lugs 186 and 188 serve as retainers to position the springs 180 and 182, and thereby more precisely define the equilibrium position of the lancet holder 132.

Figure 12:
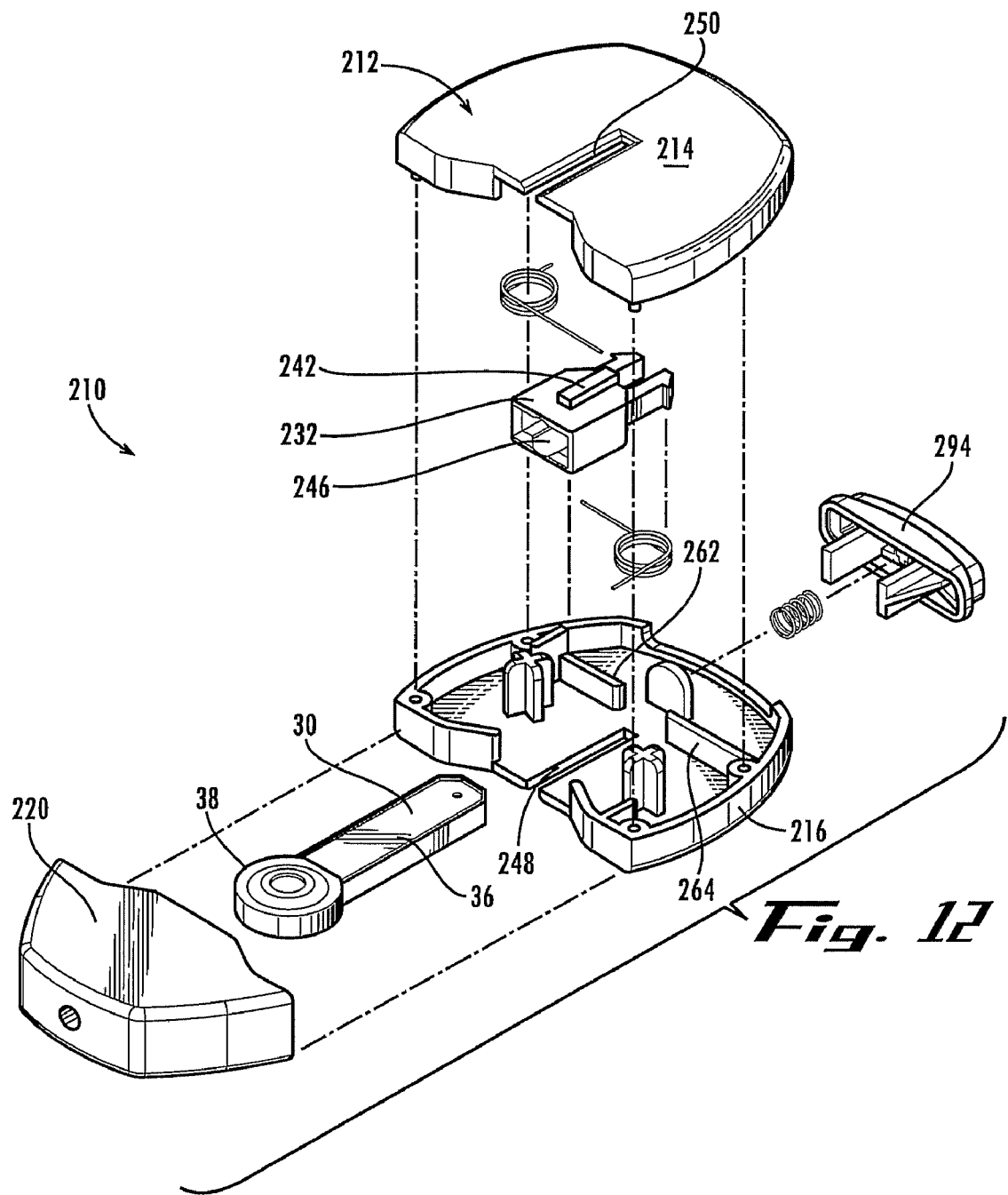
FIG. 12 is an assembly view of a multi-use lancing device according to yet another example embodiment of the present invention.

FIG. 12 depicts an alternate embodiment of the lancing device 210. The lancing device 210 is substantially similar to the lancing device 10, but with the exceptions noted herein. The lancing device 210 has a housing 212 having a top portion 214 and a bottom portion 216. A slot 250 is located within top portion 212, and a corresponding slot is located within the bottom portion 216. A lancet holder or sled 232 holds a lancet 30 securely therein. Male guide elements 242 are integrally formed on both the upper and lower surfaces of the lancet holder and extend through and slide within slots 250 and 252.

To operate the device 210, the user inserts a lancet 30 into the opening 246 of the lancet holder 232, and removes the sterility cap 38 from the lancet body 36. The user replaces the endcap portion 220. To activate the device, the user pushes (or pulls) the male guide elements 242 towards the rear of the device (i.e., towards the button 294). This in turn activates or cocks the device because the barbs 258 and 260 engage the locking tabs 262 and 264, which in turn holds the lancet holder 232 in a "ready" position.

While the invention has been described with reference to preferred and example embodiments, it will be understood by those skilled in the art that a variety of modifications, additions and deletions are within the scope of the invention, as defined by the following claims.

What is claimed is:

1. A lancing device comprising:
    a housing having first and second spring axles and at least one linear guide surface extending between the first and second spring axles;
    a lancet holder for holding a lancet and mounted for reciprocal translation along a linear lancing stroke path, the lancing stroke path being defined by the at least one linear guide surface of the housing; and
    a drive mechanism comprising a pair of torsion springs for propelling the lancet holder along the linear lancing stroke path, each of the pair of torsion springs having a coil portion carried on one of the first and second spring axles and being positioned laterally offset from the lancing stroke path of the lancet holder.

2. The lancing device of claim 1, wherein the housing has a width comparable to the length of the housing.

3. The lancing device of claim 1, further comprising a trigger to trigger the lancing stroke.

4. The lancing device of claim 3, wherein the lancet holder is barbed to hold the lancet holder in a ready position, ready for triggering.

5. The lancing device of claim 4, wherein the barbed lancet holder comprises compression arms each having at least one chamfered barb, and wherein the trigger engages the chamfered barbs to trigger the lancing stroke.

6. The lancing device of claim 1, wherein the pair of torsion springs comprises a drive spring for advancing the lancet holder along the lancing stroke and a return spring for retracting the lancet holder.

7. The lancing device as claimed in claim 1, wherein the housing is about twice as long as a lancet used therein.

8. A lancing device, comprising:
    a housing defining a linear guide path and having first and second spring axles positioned generally opposite the linear guide path from one another; and
    a drive mechanism within the housing for driving a lancet along a linear lancing stroke established by the linear guide path, the drive mechanism comprising:
        a carrier for releasably retaining the lancet;
        a first torsion spring having a coil portion mounted on the first spring axle for urging the lancet from an initial position into an extended position wherein a portion of the lancet protrudes out of the compact housing; and
        a second torsion spring having a coil portion mounted on the second spring axle for retracting the lancet back into the housing.

9. The lancing device of claim 8, further comprising a trigger for triggering the drive mechanism.

10. The lancing device of claim 8, wherein the length of the housing is between about two and four times the length of the lancet used therein.

11. A lancing device, comprising:
    a compact, non-elongated housing having first and second spring axles and defining a linear guide path between the first and second spring axles, said housing further defining a lancet opening aligned with the linear guide path;
    a drive mechanism for movably supporting a lancet along a lancing stroke constrained by the linear guide path between a retracted position within the housing and an extended position wherein a sharp tip of the lancet extends through the lancet opening, said drive mechanism further comprising a drive spring having a loop portion carried on the first spring axle and a return spring having a loop portion carried on the second spring axle;
    a trigger for triggering the drive mechanism; and
    wherein the housing has a length of no more than about four times as long as the length of the lancet used therein.

12. The housing of claim 11, wherein the housing is about twice as long as the lancet.

13. The lancing device of claim 11, wherein the housing has a width roughly equal to its length.

14. The lancing device of claim 11, wherein the housing is puck-like.

15. A lancing device comprising:
a reciprocating lancet carrier for releasably engaging a replaceable lancet, the lancet carrier traversing a linear path of travel along a forward stroke and a return stroke; and
a pair of torsion springs operating in tandem to advance the lancet carrier along the forward stroke, and to retract the lancet carrier along the return stroke, wherein a first one of the pair of torsion springs is mounted laterally offset on a first side of the linear path of travel, and wherein a second one of the pair of torsion springs is mounted laterally offset on a second side of the linear path of travel generally opposite the first side.

16. The lancing device of claim 15, wherein the pair of torsion springs comprise a drive spring and a return spring, the drive spring being stiffer than the return spring.

17. The lancing device of claim 15, wherein the lancet carrier comprises at least one arm extending therefrom, for retaining the lancet carrier in a cocked position until released by a triggering member.

18. The lancing device of claim 15, wherein the lancet carrier comprises at least one guide element for constraining motion of the lancet carrier to the linear path of travel.

19. The lancing device of claim 18, wherein free ends of the torsion springs engage against the at least one guide element to advance and retract the lancet carrier.

\* \* \* \* \*